United States Patent
Sherman

(10) Patent No.: US 6,444,225 B1
(45) Date of Patent: *Sep. 3, 2002

(54) PHARMACEUTICAL COMPOSITION COMPRISING FENOFIBRATE

(75) Inventor: Bernard Charles Sherman, 50 Old Colony Road, Willowdale, Ontario (CA), M2L 2K1

(73) Assignee: Bernard Charles Sherman, Willowdale (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/154,521

(22) Filed: Sep. 16, 1998

(30) Foreign Application Priority Data

Sep. 19, 1997  (CA) .............................................. 2214895

(51) Int. Cl.⁷ ............................ A61K 9/14; A61K 9/48; A61K 6/20; D04H 3/16
(52) U.S. Cl. ....................... 424/489; 264/115; 264/122; 424/451; 424/464
(58) Field of Search ................................. 424/489, 169, 424/456, 464, 451; 514/423, 321; 264/115, 122

(56) References Cited

U.S. PATENT DOCUMENTS

| 4,895,726 A | * | 1/1990 | Curtet et al. ................. 424/456 |
| 5,190,970 A | * | 3/1993 | Pan et al. .................... 514/423 |
| 5,545,628 A | * | 8/1996 | Deboeck et al. .............. 514/49 |
| 5,879,714 A | * | 3/1999 | Sherman ..................... 424/489 |
| 5,883,109 A | * | 3/1999 | Gregg et al. ................. 514/321 |
| 5,948,438 A | * | 9/1999 | Staniforth et al. .......... 424/464 |

* cited by examiner

Primary Examiner—Thurman K. Page
Assistant Examiner—S. Tran
(74) Attorney, Agent, or Firm—Neil H. Hughes; Ivor M. Hughes; Marcelo K. Sarkis

(57) ABSTRACT

The bioavailability of fenofibrate is improved by making a solid dispersion of a disentegrant in the fenofibrate. Method of making said solid dispersion comprising melting the fenofibrate, blending the disintegrant into the melt, and resolidifying the mixture.

5 Claims, No Drawings

PHARMACEUTICAL COMPOSITION COMPRISING FENOFIBRATE

FIELD OF INVENTION

The present invention relates to pharmaceutical compositions for oral administration comprising fenofibrate which enable improve dissolution and bioavailability.

BACKGROUND

Fenofibrate is practically insoluble in water. This causes fenofibrate to exhibit a low rate of dissolution in aqueous media (including gastrointestinal fluids), which results in inadequate bioavailability (absorption into systemic circulation) after oral ingestion.

In order to make a composition comprising fenofibrate that will enable maximum bioavailability, it is necessary to incorporate into the composition a feature that increases the rate of dissolution of the drug to enable it to dissolve in the gastrointestinal fluids.

Several ways of increasing the rate of dissolution of drugs having low solubility in water are known in the prior art.

One approach is micronization. In this approach, the drug is milled to fine particles, typically having a mean diameter of only a few microns. A second approach is to include a surfactant in the composition.

For the drug fenofibrate, neither micronization alone nor use of a surfactant alone enables maximum bioavailability. US Patent 4895726 discloses that the rate of dissolution and the bioavailability of fenofibrate can be maximized by co-micronization of fenofibrate. In this process the fenofibrate is first mixed with the surfactant and then the mixture is micronized.

A composition made according to the invention of U.S. Pat. No. 4895726 is sold in Canada as elsewhere under the tradename Lipidil Micro. The need for microcomposition and use of a surfactant adds to the cost of capsules containing fenofibrate.

In view of the limitations of the prior art, it is an object of the present invention to enable maximum bioavailability of fenofibrate without the need for micronization and without the need for use of a surfactant.

DESCRIPTION OF THE INVENTION

It has been found the rate of dissolution and the bioavailability of fenofibrate can be substantially improved by making a solid dispersion of a disintegrant in the fenofibrate. The solid dispersion can be made by heating and melting the fenofibrate, blending the disintegrant into the molten fenofibrate, and then cooling and solidifying the mixture.

Fenofibrate has a melting point of about 80° C and can be melted without decomposition.

A disintegrant will be understood to be a substance which is hydrophilic and swells upon absorption of water. Disintegrants are used as excipients (inactive ingredients) in pharmaceutical tablets and capsules so that, when a tablet or capsule is ingested, the disintegrant will cause the tablet or capsule to absorb gastrointestinal fluid and, as a result, to swell and disintegrate, so as to release the active drug for dissolution and absorption.

The most commonly used disintegrant is starch.

Disintegrants with very high capacity to absorb water and swell are known as "super-disintegrants", which include such substances as croscarmellose sodium, sodium starch glycolate and crospovidone.

As aforesaid, a solid dispersion comprising a disintegrant dispersed in the fenofibrate can be made by melting the fenofibrate, blending the disintegrant into the molten fenofibrate and then cooling and solidifying the mixture. The solid can then be ground into granules for further processing into tablets or capsules.

Because of the very intimate mixing achieved by mixing the disintegrant into the fenofibrate in the molten state, it follows that each granule or particle of the ground-up solid dispersion will be an approximately uniform mixture of fenofibrate and disintegrant.

The solid dispersion is thus intrinsically different from a mixture achieved simply by physical mixing of fenofibrate in solid form and disintegrant, because in a physical mix each particle remains either pure fenofibrate or pure disintegrant.

It will be understood that in the process of making a solid dispersion, within the scope of the present invention, ingredients other than the fenofibrate and disintegrant may be included in the molten blend and thus incorporated into the solid dispersion. Such other ingredients may include, for example, water-soluble or water-insoluble ingredients which serve as surfactant, diluent, or for other purposes.

Alternatively, other ingredients may be mixed with the granules of solid dispersion, and the mix so achieved may be further processed into tablets or capsules.

The invention will be further illustrated by the following example, which is intended to be illustrative but not limiting of the scope of the invention.

EXAMPLE 1

4800 g of fenofibrate was placed in a stainless steel pot, which was slowly heated until the fenofibrate was melted. 1200 g of croscameltose sodium was then blended into the molten fenofibrate, and the mix was then poured into trays and allowed to cool and solidify to form a solid dispersion.

The solid was then removed from the trays and milled through a #10 screen to produce granules. 5 kilos of the resulting granules were then mixed with other ingredients as follows:

| | |
|---|---|
| solid dispersion granules | 5.0 kilos |
| lactose monohydrate | 2.84 kilos |
| stearic acid | 0.14 kilos |
| colloidal silicon dioxide | 0.02 kilos |
| | 8.00 kilos |

This mixture was then filled into 2-piece hard gelatin capsules with a net fill weight of 400 mg per capsule. Each capsule thus contained 250 mg of the solid dispersion, which in turn comprised 200 mg of fenofibrate.

For these capsules, it was found that the dissolution rate and bioavailability was equivalent to that of commercially available Lipidil Micro capsules containing 200 mg of co-micronized fenofibrate and surfactant.

What is claimed is:

1. A process of making a solid pharmaceutical composition comprising a solid dispersion of a disintegrant dispersed in fenofibrate, which comprises the steps of melting the fenofibrate, blending the disintegrant into the molten fenofibrate, and solidifying the mixture.

2. The process as in claim 1 which further comprises the steps of grinding the resulting solid into granules and further processing the granules into capsules or tablets.

3. The process of claim 1 or 2 wherein the disintegrant is selected from the group consisting of croscarmellose sodium, sodium starch glycolate and crospovidone.

4. The process of claim 2 wherein each of the granules of the ground-up solid dispersion will be an approximately uniform mixture of fenofibrate and disintegrants.

5. The process of claim 3 wherein each of the granules of the ground-up solid dispersion will be an approximately uniform mixture of fenofibrate and disintegrants.

* * * * *